(12) United States Patent
Willoughby et al.

(10) Patent No.: US 8,491,551 B2
(45) Date of Patent: Jul. 23, 2013

(54) IRIS DIAPHRAGM SEAL FOR AN OSTOMY BAG

(75) Inventors: Alastair Willoughby, Cambridge (GB); Mark Rogers, North Lincs (GB); Gary Stacey, Cambridge (GB)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/697,015

(22) PCT Filed: May 10, 2011

(86) PCT No.: PCT/DK2011/050159
§ 371 (c)(1),
(2), (4) Date: Nov. 9, 2012

(87) PCT Pub. No.: WO2011/141030
PCT Pub. Date: Nov. 17, 2011

(65) Prior Publication Data
US 2013/0053803 A1  Feb. 28, 2013

(30) Foreign Application Priority Data
May 10, 2010  (DK) .................................. 2010 70198

(51) Int. Cl.
*A61F 5/44* (2006.01)
(52) U.S. Cl.
USPC ............ 604/337; 600/208; 604/338; 604/339
(58) Field of Classification Search
USPC .......................................... 604/337, 338, 339
See application file for complete search history.

(56) References Cited

U.S. PATENT DOCUMENTS

| 5,041,102 | A  | * | 8/1991 | Steer et al. ..................... 604/338 |
| 5,653,701 | A  | * | 8/1997 | Millman ........................ 604/345 |
| 6,589,167 | B1 |   | 7/2003 | Shimomura et al. |
| 7,951,125 | B2 | * | 5/2011 | Kristensen et al. ........... 604/342 |
| 2008/0132765 | A1 | * | 6/2008 | Beckman et al. ............. 600/204 |
| 2008/0146884 | A1 | * | 6/2008 | Beckman et al. ............. 600/208 |

FOREIGN PATENT DOCUMENTS

| EP | 0381393    | 8/1990  |
| GB | 2023007    | 12/1979 |
| WO | 9817212    | 4/1998  |
| WO | 9853771    | 12/1998 |
| WO | 2008103655 | 8/2008  |

* cited by examiner

*Primary Examiner* — Tatyana Zalukaeva
*Assistant Examiner* — Jordan B Bailey
(74) *Attorney, Agent, or Firm* — Coloplast Corp., Coloplast A/S; Nick Baumann

(57) ABSTRACT

A sealing wafer for use in an ostomy appliance is provided. The sealing wafer has an attachment platform with a distal surface capable of being attached to an ostomy bag, a proximal surface facing towards the user during use, and an opening having an inner boundary defining a stoma receiving opening. The sealing wafer further includes a fixed base member attached to the attachment platform and a rotating member arranged to rotate relative to the fixed base member. A sealing member is coupled between the fixed base member and the rotating member for providing a seal around a stoma and defining a stoma sealing orifice. When the rotating member is rotated relative to the base member, this rotation causes an increased or a decreased tension to be applied to the sealing member so that the diametrical dimensions of the stoma sealing orifice change from a first diameter to a second diameter. Thus a mechanical sealing member that can be used with one-piece ostomy appliances as well as with two-piece ostomy appliances is provided.

15 Claims, 2 Drawing Sheets

IRIS DIAPHRAGM SEAL FOR AN OSTOMY BAG

The invention relates to a seal for an ostomy bag which seals by means of a diaphragm contracting like an iris. Furthermore, the invention relates to an ostomy bag including such a seal.

BACKGROUND

In connection with surgery for a number of diseases in the gastro-intestinal or urinary tract, a consequence is, in many cases, that the colon, the ileum or the ureter has been exposed surgically and the patient is left with an abdominal stoma, or, in nephrostomy or ureterostomy, the ureter or a catheter is exposed in the back or the chest region or abdominal region, and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma/ureter/catheter. Also in connection with a fistula, the patient will have to rely on an appliance to collect the bodily material emerging from such opening.

Ostomy appliances are well known. Such appliances may be two-piece or one-piece appliances. In both types of appliances, an adhesive barrier member (or base plate) is attached to the wearer's abdomen/back/chest. In case of a one-piece appliance, a receiving member or bag is permanently attached to the base plate. In case of a two-piece appliance, the adhesive barrier member forms part of a body side member, and a receiving member or bag is attached releasably to the body side ostomy member for receiving exudates from the stoma. When using one-piece appliances, the whole appliance, including the adhesive skin barrier securing the appliance to the skin, is normally removed and replaced by a fresh appliance. When using two-piece appliances, the body side ostomy member is left in place up to several days, and only the receiving member or bag attached to the body side member is replaced. The attachment means for attaching an ostomy receiving bag may for example be a system known per se comprising matching coupling rings or matching flanges and adhesive surfaces engaging with and sealing against a flange area of the body side member.

It is necessary to change the body side member of a two-piece appliance when the centre part of the adhesive wafer has deteriorated to such a degree as to allow access of the aggressive exudates to the skin surrounding the stoma, irrespective of the fact that the wafer as such has a much longer wearing time. The access of aggressive exudates to the skin is causing skin problems. Frequent changing of the body side member of a two-piece appliance is undesirable due to the irritation of the skin, and the quality of life of the user may be improved and the nuisance of the wearing of an ostomy appliance reduced if the intervals between replacing the body side member can be increased The service time of the body side ostomy member depends inter alia on the amount and the aggressiveness of the exudates and of the sealing between the stoma and the body side ostomy member. The sealing depends on the fit to the stoma. Conventionally, only a limited number of standard appliances having holes of different sizes are available and the user, or an assistant, must customise the body side member by cutting the edge of the hole to adapt the body side member to the stoma.

When cutting the edge of the hole of an adhesive wafer of a conventional one-piece ostomy appliance for adapting it to the size and shape of a stoma, the cutting is complicated by the fact that, in order to secure discretion, for decorative purposes and for providing softness, low noise generation and comfort, the bag is often made from an opaque material or covered and/or provided with a cover or front layer rendering it very difficult, if not impossible for the user or the nurse to observe the stoma area during determination of a cutting line, for adaptation of the hole or when applying the appliance.

SUMMARY OF THE INVENTION

The invention concerns a seal in a wafer for an ostomy appliance. The seal comprises two parts rotatable with respect to each other (a fixed member and a rotating member) and a sealing member disposed there between. When the rotating member is rotated with respect to the fixed member, the sealing member is deformed and an inner diameter of the sealing member is increased. Thereby a mechanical sealing member is achieved, which makes it possible to use the sealing member with one-piece ostomy appliances as well as two-piece ostomy appliances.

DETAILED DESCRIPTION OF THE INVENTION

In a first aspect, the invention relates to a sealing wafer for use in an ostomy appliance comprising an attachment platform having a distal surface capable of being attached to an ostomy bag, a proximal surface facing towards the user during use, and an opening having an inner boundary defining a stoma receiving opening, a fixed base member attached to the attachment platform, a rotating member arranged to rotate relative to the fixed base member, a sealing member coupled between the fixed base member and the rotating member for providing a seal around a stoma and defining a stoma sealing orifice, wherein a rotation of the rotating member relative to the base member causes a difference in tension of the sealing member so that the diametrical dimensions of the stoma sealing orifice change from a first diameter to a second diameter.

As the sealing member is coupled between the fixed base member and the rotating member, the rotation of the rotating member relative to the base member ensures that the force required to rotate is transferred to the sealing member in the form of a tension within the sealing member, as the sealing member is connected between the two members, and this transferred tension causes the sealing member to contract or expand from a first diameter to a second diameter of the stoma sealing orifice.

When the fixed base member and the rotation member are in a neutral position relative to each other, the applied tension within the sealing member is negligible, and the sealing member is in its most expanded configuration, maintaining the stoma sealing orifice in its most constricted position, i.e. in its smallest diameter. Any rotational force applied to the rotation member causes tension in the sealing member between the rotating member and the fixed base member, where the tension causes the sealing member to stretch in the direction of the rotation resulting in some of the material of the sealing member to be moved relative to the fixed base member, causing the stoma sealing orifice to expand, resulting in an increased diameter of the stoma receiving opening.

The above provides a sealing wafer which is particularly suitable for use with a stoma, as one of the most challenging issues facing the users is to ensure that no leaks occur between the stoma and an ostomy wafer, because the stoma output may be seen as very unhealthy for the skin surrounding the stoma. Thus, by providing a resilient sealing member capable of being adapted to fit snugly around the stoma, it is possible to reduce the risk that liquefied exudates from the stoma come into contact with the skin surrounding the stoma.

Moreover, such a sealing wafer can be used for many different sizes and types of uneven skin surfaces around a stoma, and thus the need to provide many different sealing wafers in order to accommodate many different stomas is significantly reduced.

In one embodiment of the present invention, the first diameter of the stoma sealing orifice is larger than the second diameter of the stoma sealing orifice. In this way, the tension applied to the sealing member, as described above, has been applied prior to the use of the sealing wafer. Thus, the user can apply the sealing wafer around the stoma and decrease the diameter of the sealing member using the rotating member, until the stoma sealing orifice is of a suitable dimension to fit around the stoma, while providing a seal around it.

In one embodiment of the present invention, the first diameter of the stoma sealing orifice is smaller than the second diameter of the stoma sealing orifice. In this way, the base member and the rotation member, as described above, may be in a neutral position relative to each other, meaning that there is no tension within the sealing member. Thus, by applying rotational forces to the rotation member, the dimensions of the stoma sealing orifice may be increased during application, until the stoma sealing orifice is of a suitable dimension to fit around the stoma, while providing a seal around it.

In another embodiment, the dimensions of the stoma receiving orifice may be increased or decreased at will, so that a continuous adjustment may be made to ensure that the sealing member provides an effective seal around the stoma.

In one embodiment of the present invention, the wafer may comprise a locking means for fixing the position of the rotating member relative to the base member. The provision of locking means ensures that when the user has found the correct dimension of the stoma receiving orifice, the sealing member may be locked in the correct dimension so that the rotation member does not rotate towards its neutral position due to the tension in the sealing member which may constrict the stoma or so that it does not rotate in the opposite direction involuntarily causing the seal between the sealing member and the stoma to break.

In one embodiment of the present invention, the locking means may be in the form of a control member. The control member, or the control ring, may be attached to the fixed base member so that the control ring member is rotationally fixed relative to the fixed base member, where the control ring engages the rotation member so that the rotation member may be locked in its position relative to the fixed base member. Alternatively, the control member may be fixed in position relative to the rotational member and rotate along with the rotation member relative to the base member, where the control member may engage the base member for locking the rotation member in its position.

In one embodiment of the present invention, the base member may have means, such as a set of lugs, which enable the control member to be attached to it in a number of rotational positions. Thus, the control member may rotate relative to the base member until the means or the lugs engage with a matching means in the control member, such as holes, for fixing it in position relative to the base member. By doing this, it is possible to have the fixed base member, the rotation member and/or the control member rotating independently of each other, and allowing each member to be locked in place at a predetermined position.

In one embodiment of the present invention, the base member and the rotating member may be arranged having a ratchet enabling click-wise rotation of the rotating member relative to the base member. This click-wise rotation ensures that the user may rotate the rotating member incrementally, without having visual confirmation about the position of the rotational member. The click function may be felt or heard during the rotation, so that the user knows when the rotation member has been moved a specific distance. This is advantageous when the user needs to adjust the sealing member in a public place so that he/she does not have to remove clothing to adjust the seal between the sealing member and the stoma.

In one embodiment of the present invention, the sealing member may be an elastomer membrane, sheet or tube. By using a membrane sheet or a tube, the sealing member may be folded in such a way that a first peripheral end of the proximal side member of the sealing member superimposes a second peripheral end of the distal side member of the sealing member, and the folding line or folding bend between the proximal and the distal side members defines the stoma sealing opening. Thus, when the rotation member is rotated relative to the base member, the proximal and the distal side member slide relative to each other and causes the folding line or the folding bend to move in a radial direction relative to the fixed base member and/or the rotational member.

In one embodiment of the present invention, the elastomer may be a Silicone, rubber, polymer, thermoplastic elastomer, a Dow Corning 30 Shore A silicone type, thermoplastic polyurethane or any suitable elastomeric material. The suitability of the elastomeric material depends on how well the material tolerates output from the stoma. The flexibility and resilience of the material ensuring that the tension applied to the material does not permanently deform the material, thus ensuring that the material will return to its natural position when no tension is applied to the material. The specific choice of material may be obvious to the skilled person, based on the teachings of the present invention.

In one embodiment of the present invention, the base member may further comprise means, such as a recess, for attaching a first end of the sealing member to the base member. This ensures that the sealing member is attached to the base member and will not involuntarily release during use. Furthermore, such means may be used in such a way where the sealing member may be realisably attached to the base member so that either the sealing member may be replaced reusing the base member and the remaining parts of the sealing wafer or the base member and the remaining parts of the sealing wafer may be replaced reusing the sealing member in a different sealing wafer.

In one embodiment of the present invention, the rotating member may further comprise means, such as a recess, for attaching a second end of the sealing member to the base member. This ensures that the sealing member is attached to the rotation member, and will not involuntarily release during use. Furthermore, such means may be used in such a way where the sealing member may be realisably attached to the rotation member so that either the sealing member may be replaced reusing the base member and the remaining parts of the sealing wafer or the rotation member and the remaining parts of the sealing wafer may be replaced reusing the sealing member in a different sealing wafer, similar to what is described in the above paragraph.

In one embodiment of the present invention, the base member may further have an inner lip member preventing the separation of the rotating member from the base member and enabling the rotating member to engage with the base member so that the two members may rotate freely with respect to one another and to be able to transfer loads other than torque around the axis between the two members.

Within the meaning of the present invention, it should be understood that the tension applied to the sealing member by rotating the rotating member relative to the base member is substantially the same or similar to the transfer of a load in the form of torque around an axis between the rotation member and the base member and the terms should be understood as synonyms.

A second aspect of the invention relates to an ostomy appliance comprising a sealing wafer as described above, and an ostomy collecting bag attachable to the distal surface of the attachment platform.

In one embodiment of the ostomy appliance, the ostomy collecting bag may be attached to the distal surface of the attachment platform by an adhesive coupling.

In one embodiment of the ostomy appliance, the ostomy collecting bag may be attached to the distal surface of the attachment platform by a mechanical coupling.

This invention relates specifically to the sealing wafer, but also to ostomy appliances that contain such a seal. Although the following description sets out the design of a seal for a two piece appliance it should be understood that the same principle can be applied to the design of a one-piece appliance.

Such an ostomy collecting bag may be attached to the distal surface of the attachment platform by for example an adhesive coupling or a mechanical coupling. Alternatively, the ostomy collecting bag may be permanently attached during manufacturing by for example a weld or glue.

The invention provides users with a seal for their ostomy bag with only a single size covering all sizes and shapes of stoma without the need to use a tool such as a scalpel to reshape the device.

The invention further provides users with a sealing wafer that can be adjusted to fit once the user platform is in place.

The invention further provides users with a sealing wafer that can be adjusted once the bag is in place and during wear.

The invention further provides users with a sealing wafer that has adjustment limits so that it is not so tight as to constrict blood flow as this is potentially fatal.

The invention further provides users with a sealing wafer and user platform in which loads associated with the bag element of the total appliance containing stoma discharge can be passed to the user platform Typically, the attachment platform is in the shape of a disc having a relative large surface area in relation to its thickness. The disc can have many shapes, typically annular and circular, but may also have a square, triangular or ellipsoidal shape.

DETAILED DESCRIPTION

Figure 1:
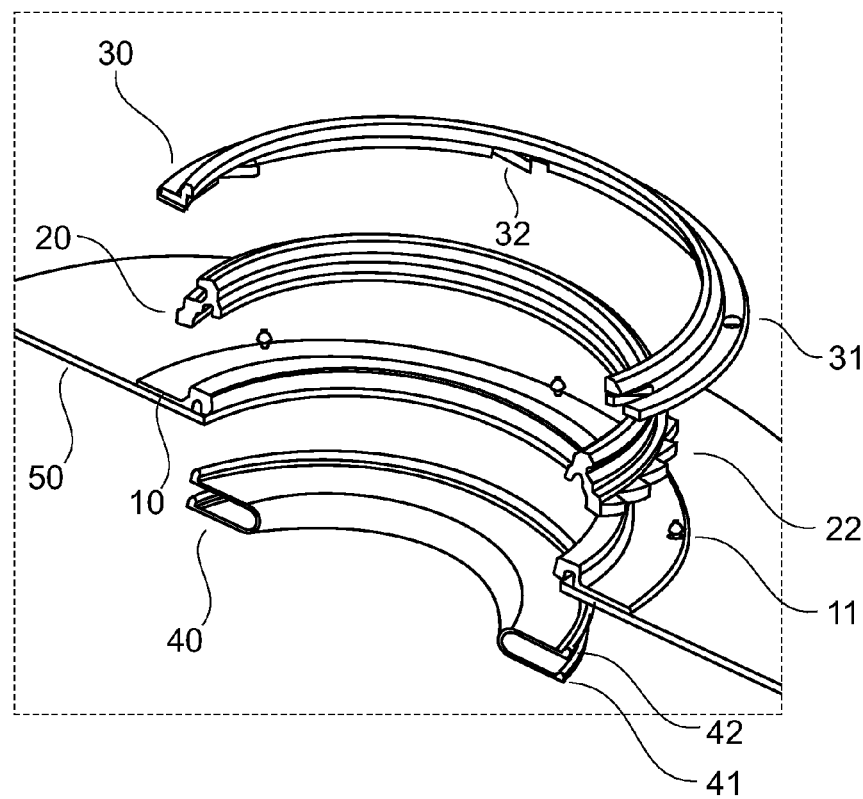
FIGS. 1, 2 and 3 show one embodiment of the sealing wafer according to the invention in section.
Figure 2:
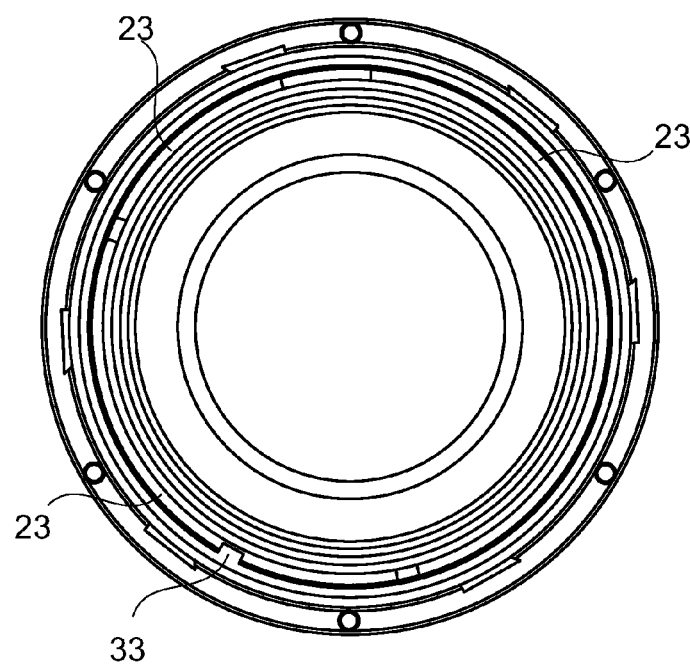
Figure 3:
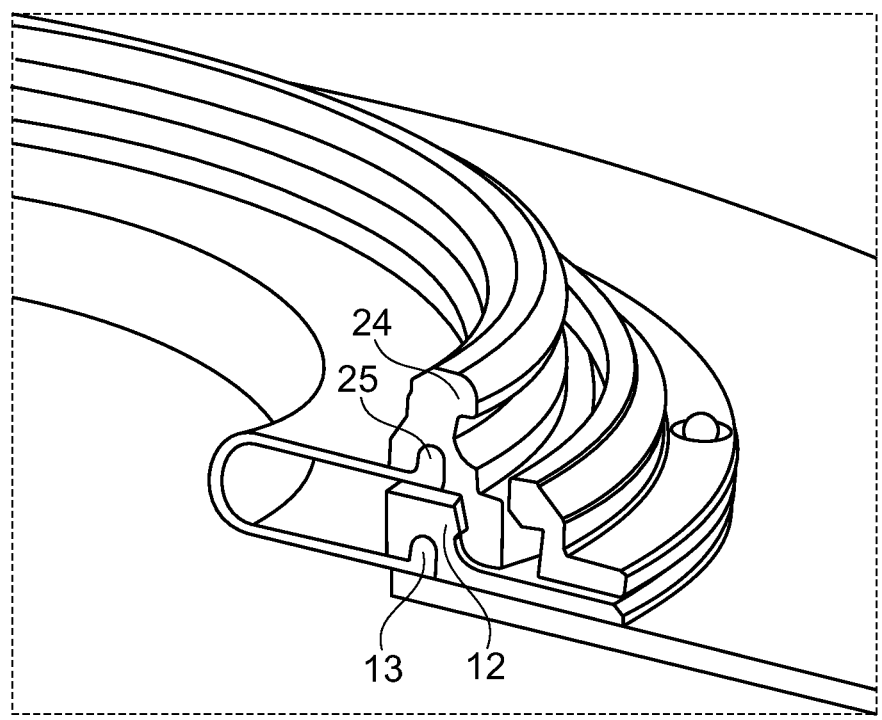

One embodiment of a sealing wafer arranged in an ostomy base plate is shown in FIGS. 1, 2 and 3. The embodiment is shown in section along a symmetry line of both the sealing wafer and the base plate in FIGS. 1 and 2, and the sealing wafer is shown from the distal surface in FIG. 3.

Herein, the distal side/surface should be understood as being a part of an element facing away from the body when the ostomy device is placed around the stoma, while any reference to a proximal side/surface should be understood as being part of an element facing towards the body during use.

The ostomy appliance comprises an ostomy base plate 50, a sealing wafer and a collection bag (not shown). A base ring 10 is connected to the ostomy base plate 50. The base ring has a set of lugs or knobs 11 which enables a control ring 30 to be later attached to it in a number of rotational positions. The base ring 10 also has a feature 13 such as a recess that enables a proximal end of an elastomer tube 41 to be attached to it. Such an elastomer may be selected from the group consisting of SEBS (styrene ethylene butylene styrene block copolymer), SBS (styrene butadiene styrene block copolymer), SIS (styrene isoprene styrene block copolymer) and TPO (which is a mixture of PP (polypropylene), PE (polyethylene) and non cross-linked EPDM (ethylene propylene diene monomer) rubber).

The base ring 10 also has an inner lip 12 that enables a rotating ring 20 to engage with it so that the two rings may rotate freely with respect to one another but not be separated from each other in the axial direction, i.e. in a direction that is defined by an axis that intersects the centre of the two rotating rings.

The rotating ring 20 has an outer lip 21 which provides the engagement with the inner lip 12 of the base ring to perform these functions. The rotating ring 20 has a set of tooth features 22 integral to it that defines the rack element of the ratchet. In addition, it has several slots 23 of various lengths around the periphery into which the nub 33 on the control ring 30 will fit at the point where the control ring is engaged. The rotating ring 20 has a feature 25 coupling zone, such as a depression or a protrusion, onto which the distal end 42 of the elastomer tube 40 is connected in such a way as to form a joint that is impermeable to stoma discharge materials. The rotating ring 20 has a coupling ring 24 onto which an ostomy collection bag is attached. The coupling ring is formed to receive a corresponding coupling ring (not shown) arranged on an ostomy collecting bag (not shown).

The control ring 30 has a set of features such as shaped holes 31 that engage with the lugs 11 on the base ring 10. The control ring 30 also has a nub feature 33 which engages with one of the slots 23 on the rotating ring 20. These hole features 31 and the lugs 11 on the base ring are distributed around the rings in such a way that the control ring 30 may be engaged with the base ring 10 in one of a number of rotational positions. Each of these positions corresponds with the nub 33 of the control ring 30 aligning with a different slot 23 on the rotating ring 20. Thus, the control ring 30 once engaged with the base ring 10 provides limits to the rotational movement of the rotating ring 20. The holes 31 and lugs 11 are so shaped that once the control ring 30 has been engaged onto the base ring 10, the lugs 11 may not be withdrawn from the holes 31.

In order to hold the sealing closed, the control ring 30 also has a set of features 32 that functions as the pawls of the ratchet. These features are positioned on the control ring 30 so that it will only engage with the rack element 22 of the ratchet when the control ring 30 has been engaged onto the base ring 10. This ensures that the ratchet cannot lock the base ring 10 and rotating ring 20 in a particular position unless the control ring 30 has been engaged. The control ring 30 has multiple pawl elements 32, which are arranged around the surface of the ring to engage with the rack. These elements are offset by a fraction of the rack pitch so that finer control of the rotation locking position of the base and rotating ring can be achieved.

The elastomer tube 40 is attached at each end to the base ring 10 and rotating ring 20. These connections are of a type that is impermeable to stoma discharge materials and other fluids. In addition, these connections are of a sufficient quality for them to remain attached to the base and rotating ring when the rings are rotated with respect to one another. The elastomer sheet is made from a material such as latex that is impermeable to effluents from the stoma and capable of being deformed elastically. The elastomer tube is of such a length that when it is engaged to the base and rotating ring, there is a flap of material formed to the interior of the rings. The end of this flap of material forms an orifice at the centre of the rings. The appliance operates essentially by rotating the rotating ring with respect to the base ring. This causes the central orifice to contract diametrically as the elastomer sheet is stretched. The appliance is supplied integrated with the user platform 50. When the user platform is affixed to the ostomate, the control ring is rotated to a selected position.

This position is chosen to engage the nub in a chosen slot on the rotating ring. The control ring is then affixed to the lugs on the base ring. The nub in the slot limits the relative rotation of the base ring and rotating ring, and therefore limits the variation in orifice size available. Thus, the device is prevented from being over-tightened onto the stoma. Further, as supplied, the control ring and the pawls are not engaged with the rack on the rotating ring. These only become engaged when the control ring is secured onto the base ring. Thus, the device cannot be over-tightened permanently before the control ring is secured in place.

Once the device is in place and the control ring secured in place on the base ring, the rotating ring is rotated against the ratchet until the orifice has closed sufficiently around the stoma to form a seal. Thus, the user platform and seal device are now ready for the discharge collection bag to be attached and the complete stoma discharge system completed.

The invention claimed is:

1. A sealing wafer for use in an ostomy appliance, comprising
   an attachment platform having a distal surface attached to an ostomy bag, a proximal surface facing towards the user during use, and an opening have an inner boundary defining a stoma receiving opening,
   a fixed base member attached to the attachment platform,
   a rotating member arranged to rotate relative to the fixed base member,
   a sealing member coupled between the fixed base member and the rotating
   member for providing a seal around a stoma and defining a stoma sealing orifice,
   wherein a rotation of the rotating member relative to the base member causes an increased or a decreased tension to be applied to the sealing member so that the diametrical dimensions of the stoma sealing orifice change from a first diameter to a second diameter.

2. A sealing wafer according to claim 1, wherein the first diameter of the stoma sealing orifice is larger than the second diameter of the stoma sealing orifice.

3. A sealing wafer according to claim 1, wherein the first diameter of the stoma sealing orifice is smaller than the second diameter of the stoma sealing orifice.

4. The wafer according to claim 1, wherein the wafer comprises locking means for fixing the position of the rotating member relative to the base member.

5. The wafer according to claim 1, wherein the locking means are in the form of a control member.

6. The wafer according to claim 5, wherein the base member has means, such as a set of lugs, which enable the control member to be attached to it in a number of rotational positions.

7. The wafer according to claim 1, wherein the base member and the rotating member are arranged having a ratchet enabling clock-wise rotation of the rotating member relative to the base member.

8. The wafer according to claim 1, wherein the sealing member is an elastomer membrane, sheet or tube.

9. The wafer according to claim 1, wherein the elastomer is a silicone, rubber, thermoplastic elastomer, a Dow Corning 30 Shore A silicone type or any other suitable elastomeric material, or a combination/blend thereof.

10. The wafer according to claim 1, wherein the base member further comprises means, such as a recess, for attaching one end of the sealing member to the base member.

11. The wafer according to claim 1, wherein the rotating member further comprises means, such as a recess, for attaching a second end of the sealing member to the base member.

12. The wafer according to claim 1, wherein the base member further has an inner lip member preventing the separation of the rotating member from the base member and enabling the rotating member to engage with the base member so that the two members may rotate freely with respect to one another and to be able to transfer loads other than torque around the axis between the two members.

13. An ostomy appliance comprising a sealing wafer according to claim 1 and an ostomy collecting bag attachable to the distal surface of the attachment platform of the sealing wafer.

14. An ostomy appliance according to claim 13, wherein the ostomy collecting bag is attached to the distal surface of the attachment platform by an adhesive coupling.

15. An ostomy appliance according to claim 13, wherein the ostomy collecting bag is attached to the distal surface of the attachment platform by a mechanical coupling.

* * * * *